United States Patent
Matsuda et al.

(10) Patent No.: US 9,983,113 B2
(45) Date of Patent: May 29, 2018

(54) PARTICLE COUNTER

(71) Applicant: RION CO., LTD., Tokyo (JP)

(72) Inventors: Tomonobu Matsuda, Tokyo (JP); Masaki Shimmura, Tokyo (JP); Mitsuaki Saitou, Tokyo (JP); Yuki Yamakawa, Tokyo (JP)

(73) Assignee: RION CO., LTD., Tokyo (JP)

( * ) Notice: Subject to any disclaimer, the term of this patent is extended or adjusted under 35 U.S.C. 154(b) by 0 days. days.

(21) Appl. No.: 15/365,096

(22) Filed: Nov. 30, 2016

(65) Prior Publication Data

US 2017/0160178 A1 Jun. 8, 2017

(30) Foreign Application Priority Data

Dec. 3, 2015 (JP) ................. 2015-236987

(51) Int. Cl.
*G01B 9/02* (2006.01)
*G01N 15/06* (2006.01)
*G01N 15/02* (2006.01)
*G01N 15/14* (2006.01)

(52) U.S. Cl.
CPC ......... *G01N 15/06* (2013.01); *G01B 9/02024* (2013.01); *G01B 9/02038* (2013.01); *G01N 15/0211* (2013.01); *G01N 15/1434* (2013.01); *G01N 15/1459* (2013.01); *G01N 2015/0687* (2013.01); *G01N 2015/0693* (2013.01); *G01N 2015/1454* (2013.01); *G01N 2015/1486* (2013.01)

(58) Field of Classification Search
CPC ..... G01N 15/06; G01N 21/00; G01B 9/02038
See application file for complete search history.

(56) References Cited

U.S. PATENT DOCUMENTS

2004/0011974 A1* 1/2004 Matsuda ............ G01N 15/1436
250/574
2011/0001969 A1 1/2011 Nakamura
(Continued)

FOREIGN PATENT DOCUMENTS

| JP | 2003270120 A2 | 9/2003 |
| JP | 2011013162 A1 | 1/2011 |
| JP | 5438198 B1 | 3/2014 |

*Primary Examiner* — Jonathan Hansen
(74) *Attorney, Agent, or Firm* — Rankin, Hill & Clark LLP

(57) ABSTRACT

Provided is a particle counter including: a light source; a light superimposition unit configured to superimpose light beams; an irradiation optical system configured to irradiate a fluid in a flow passage with one of a plurality of light beams from the light source; a detection optical system configured to make a part of scattered light beams by a particle in the fluid enter the light superimposition unit; a reference optical system configured to split another one of the plurality of light beams into a plurality of reference light beams and makes the reference light beams enter the light superimposition unit; and a counting unit configured to count the particles on the basis of detection signals corresponding to an interference light beam received by a light receiver. The interference light beam is generated by interference between the scattered light beam and one of the reference light beams at the light superimposition unit, and is received by the light receiver corresponding to the reference light beam.

18 Claims, 6 Drawing Sheets

(56) References Cited

U.S. PATENT DOCUMENTS

| | | | |
|---|---|---|---|
| 2011/0249255 A1* | 10/2011 | Bentien | G01N 15/1434 356/51 |
| 2012/0133936 A1* | 5/2012 | Imai | G01N 15/1429 356/338 |
| 2014/0152986 A1* | 6/2014 | Trainer | G01N 15/0205 356/336 |

* cited by examiner

PARTICLE COUNTER

CROSS-REFERENCE TO RELATED APPLICATION

This application claims priority from Japanese Patent Application No. 2015-236987 filed with the Japan Patent Office on Dec. 3, 2015, the entire contents of which are hereby incorporated by reference.

BACKGROUND

1. Technical Field

The present disclosure relates to a particle counter.

2. Related Art

Particle counters are known as devices for measuring particles in fluids which are, for example, liquids such as a chemical solution and water, or gas such as air. At the particle counter, a fluid containing particles is irradiated with a laser beam. Scattered light from the particles in the irradiated fluid is observed to count the particles (for example, refer to Japanese Patent No. 5438198).

For example, in the manufacture of semiconductor wafers, the particles of impure substances contained in the chemical solution to be used exert influence on the manufacturing process. Accordingly, a particle counter is used to count the particles in the chemical solution to control the state of the chemical solution. However, scattered light (background light) is generated by the medium of the chemical solution (that is, the chemical solution itself). Thus, measuring particles in the chemical solution involves larger background noise than that in the case of measuring the particles in the water. This makes it difficult to count small-size particles (for example, 30 nm or less).

One particle counter uses a multi-divided light receiving element. The multi-divided light receiving element reduces the effective light receiving areas at end portions. As a result, reducing the noise resulting from the background light improves the signal-to-noise (S/N) ratio (for example, refer to Japanese Patent No. 5438198).

Meanwhile, there has been proposed a dynamic light-scattering measuring device having a Mach-Zehnder interferometer and a low-coherence light source (for example, refer to JP-A-2011-13162). Such a dynamic light-scattering measuring device determines particle size distribution on the basis of changes in scattered light intensity resulting from Brownian motion of the particles.

SUMMARY

A particle counter according to an embodiment of the present disclosure includes: a light source; a light superimposition unit configured to superimpose two light beams travelling in a space; an irradiation optical system configured to irradiate a fluid flowing in a flow passage with one of a plurality of light beams obtained by splitting a light beam from the light source to form a detection area; a detection optical system configured to make a scattered light beam with a different direction from the optical axis of the irradiation optical system enter the light superimposition unit, out of scattered light beams scattered by a particle contained in the fluid in the detection area; a reference optical system configured to split another one of the plurality of light beams into a plurality of reference light beams travelling in a space and makes the reference light beams enter the light superimposition unit; a detector comprising light receivers, each light receiver being corresponding to each of the reference light beams, and configured to generate detection signals corresponding to an interference light beam received by the light receiver; and a counting unit configured to count the particles on the basis of the detection signals. The interference light beam is generated by interference between the scattered light beam and one of the reference light beams that enter the light superimposition unit, and is received by the light receiver corresponding to the reference light beam.

DETAILED DESCRIPTION

Figure 1:
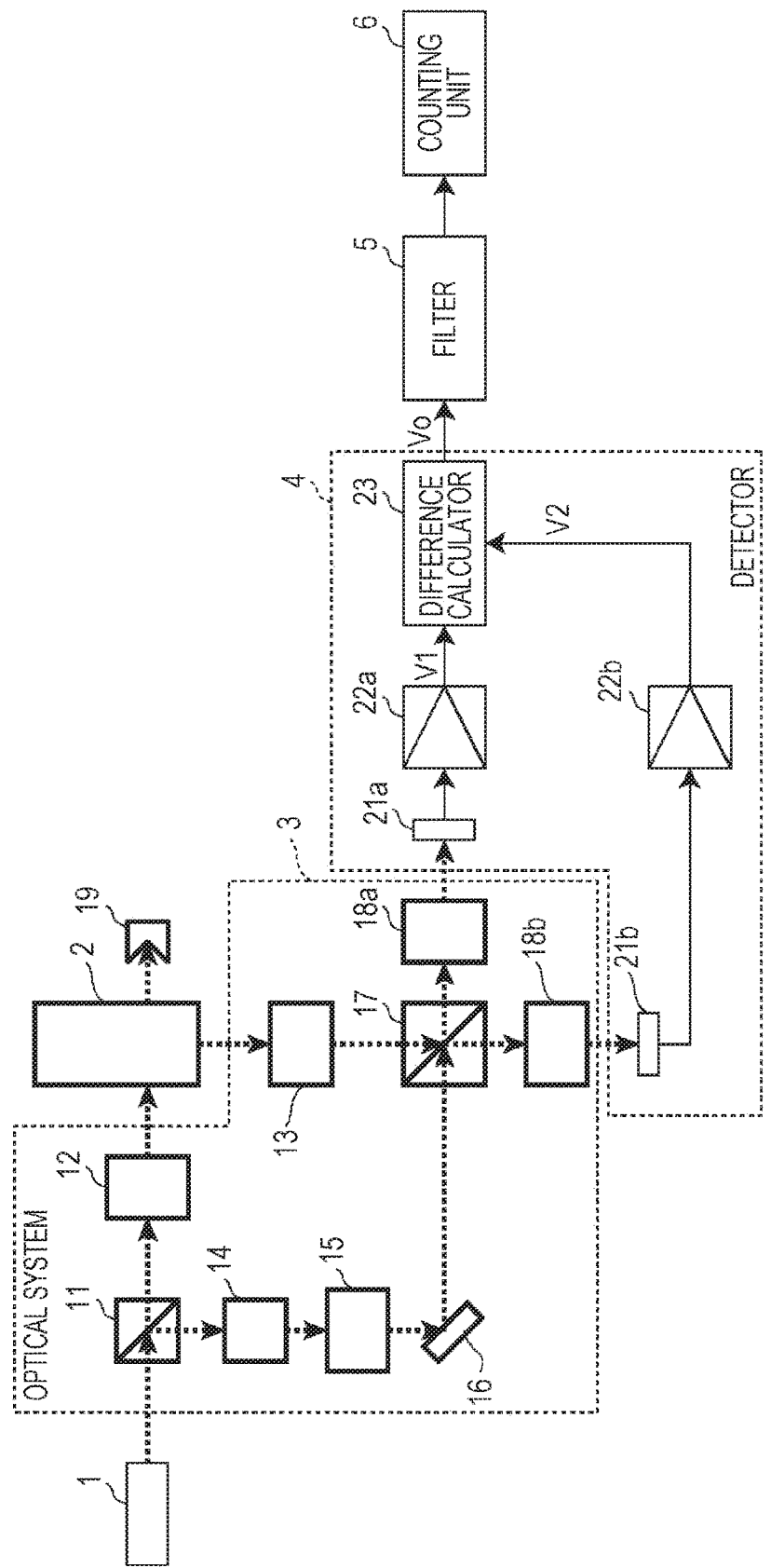
FIG. 1 is a block diagram illustrating a structure of a particle counter according to a first embodiment of the present disclosure.

In the following detailed description, for purpose of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

The foregoing dynamic light-scattering measuring device can determine particle size distribution. However, this device uses Brownian motion of the particles and is not suited for counting particles in a fluid.

The foregoing particle counter can count some particles with small sizes. However, there is need for counting particles with still smaller sizes. For example, according to the refinement of manufacturing process based on technical progress in the manufacture of semiconductor wafers in recent years, there has been demand for particle counters that is capable of counting particles with particle sizes of 30 nm or less.

In light of the foregoing problems, an object of the present disclosure is to provide a particle counter that is capable of counting small-size particles in a fluid at favorable S/N ratios.

A particle counter according to the present disclosure includes: a light source; a light superimposition unit configured to superimpose two light beams travelling in a space; an irradiation optical system configured to irradiate a fluid flowing in a flow passage with one of a plurality of light beams obtained by splitting a light beam from the light source to form a detection area; a detection optical system configured to make a scattered light beam with a different direction from the optical axis of the irradiation optical system enter the light superimposition unit, out of scattered light beams scattered by a particle contained in the fluid in the detection area; a reference optical system configured to split another one of the plurality of light beams into a plurality of reference light beams travelling in a space and makes the reference light beams enter the light superimposition unit; a detector comprising light receivers, each light receiver being corresponding to each of the reference light beams, and configured to generate detection signals corresponding to an interference light beam received by the light receiver; and a counting unit configured to count the particles on the basis of the detection signals. The interference light beam is generated by interference between the scattered light beam and one of the reference light beams that enter the light superimposition unit, and is received by the light receiver corresponding to the reference light beam.

According to the present disclosure, it is possible to count small-size particles at favorable S/N ratios. In addition, a plurality of reference light beams is used in the present disclosure. Accordingly, it is possible to provide a particle counter that has a wider detection area and a higher counting efficiency than the detection area and the counting efficiency of particle counters with the use of only one reference light beam.

Embodiments of the present disclosure will be explained below with reference to the drawings.

First Embodiment

FIG. 1 is a block diagram illustrating a structure of a particle counter according to a first embodiment of the present disclosure. The particle counter illustrated in FIG. 1 has a light source 1, a flow cell 2, an optical system 3, a detector 4, a filter 5, and a counting unit 6.

The light source 1 emits a light beam (a laser beam in this example) with a predetermined wavelength. In the embodiment, the light source 1 emits a high-coherence single-mode light beam. For example, the light source 1 may be a laser light source with a wavelength of 532 nm and an output of about 1000 mW.

The flow cell 2 includes a flow passage for a fluid containing particles to be counted. In the embodiment, the fluid containing particles to be counted may be a liquid.

Figure 2:
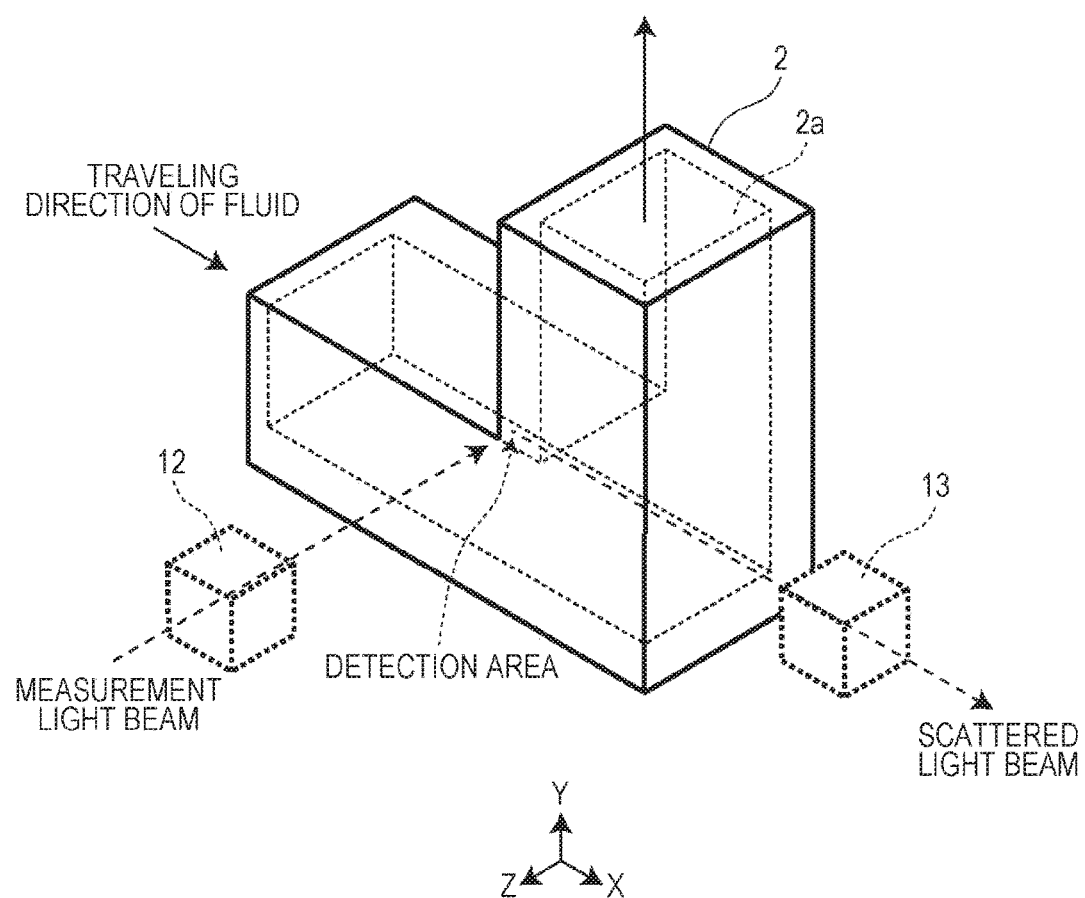
FIG. 2 is a perspective view of an example of a flow cell 2 illustrated in FIG. 1.

FIG. 2 is a perspective view of an example of the flow cell 2 illustrated in FIG. 1. As illustrated in FIG. 2, the flow cell 2 is bent in an L shape. That is, the flow cell 2 may be a transparent member that forms a bent flow passage 2a. When the fluid containing particles to be counted is a chemical solution such as isopropyl alcohol, hydrofluoric acid solution, or acetone, the sapphire flow cell 2 is used, for example.

In the flow cell 2, the fluid flowing in the flow passage 2a is irradiated with one of light beams obtained by splitting a light beam from the light source 1 to form a detection area.

The optical system 3 includes a beam splitter 11, an irradiation optical system 12, a detection optical system 13, an attenuator 14, a diffraction optical system 15 as a reference optical system, a unit including a mirror 16 and a beam splitter 17 as a light superimposition unit, and condensers 18a and 18b.

The beam splitter 11 splits a light beam from the light source 1 into two. One of the light beams split by the beam splitter 11 (hereinafter, called measurement light beam) enters the irradiation optical system 12. The other of the light beams split by the beam splitter 11 (hereinafter, called reference light beam as appropriate) enters the attenuator 14. For example, the beam splitter 11 splits the light beam from the light source 1 at a predetermined uneven ratio (for example, 90:10). Accordingly, the intensity of the measurement light beam is larger than the intensity of the reference light beam.

The irradiation optical system 12 irradiates the fluid flowing in the flow passage 2a with the measurement light beam from a direction (in this example, the vertical direction, that is, Z direction in FIG. 2) different from a travelling direction of the fluid in the flow passage 2a of the flow cell 2 (X direction in FIG. 2). The irradiation optical system 12 may be a lens group as described in JP-A-2003-270120, for example, that shapes the laser beam in such a manner as to enhance its energy density.

The foregoing irradiation of the measurement light beam generates the scattered light beams by the particles in the flow passage 2a. The detection optical system 13 makes the scattered light beams by the particles enter a predetermined incident surface of the beam splitter 17. For example, the detection optical system 13 includes a condensing lens. Alternatively, the detection optical system 13 includes a pin hole for blocking background light and condensing lenses arranged on the front and back sides of the pin hole.

In the embodiment, the measurement light enters the flow passage 2a from a direction different from the optical axis of the detection optical system 13. Accordingly, the detection optical system 13 makes the scattered light beam resulting from side scattering enter the beam splitter 17.

Figure 3:
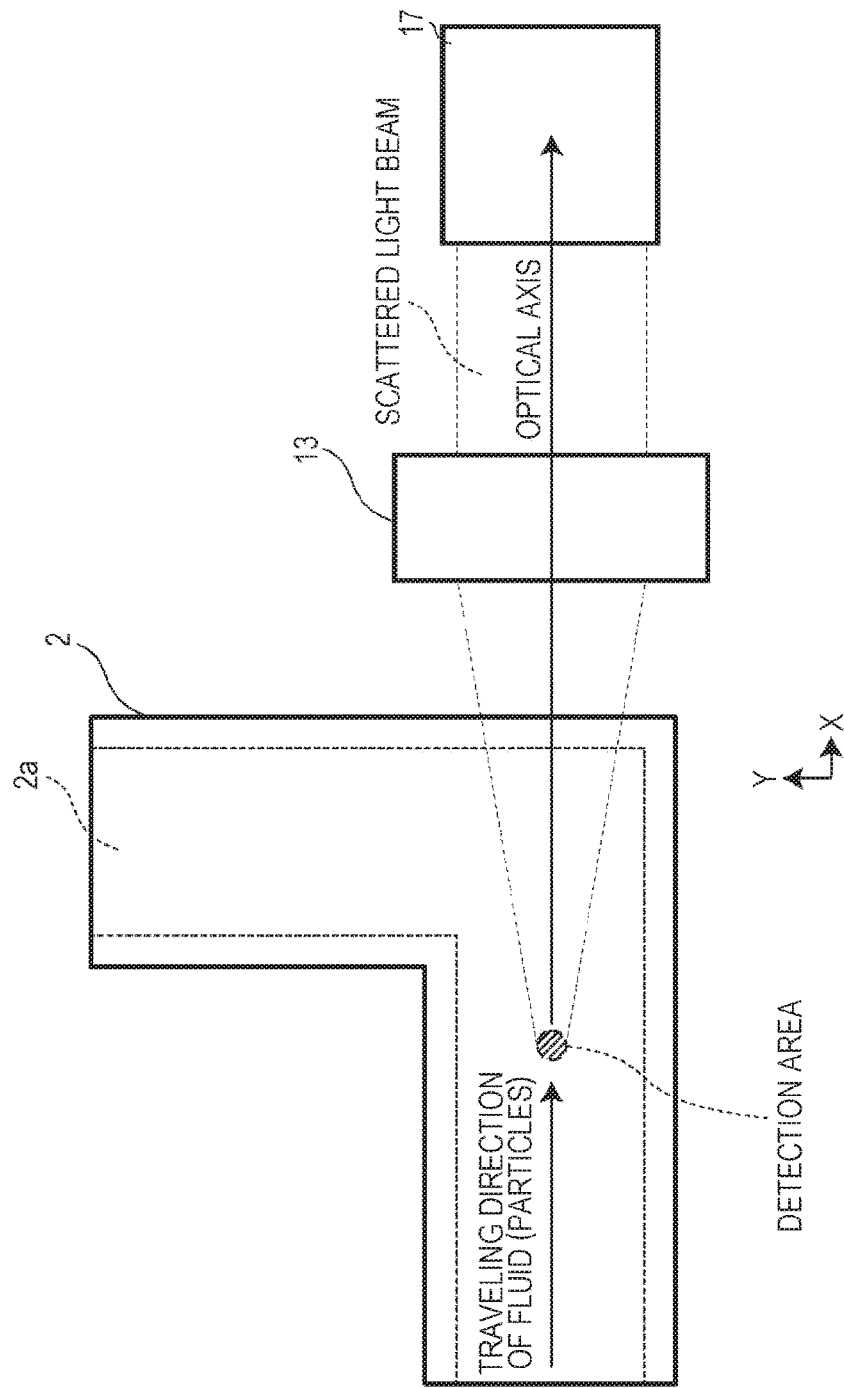
FIG. 3 is a side view for describing the arrangement of the flow cell 2, a detection optical system 13, and a beam splitter 17 illustrated in FIG. 1.

FIG. 3 is a side view for describing the arrangement of the flow cell 2, the detection optical system 13, and the beam splitter 17 illustrated in FIG. 1. Specifically, as illustrated in FIG. 3, the detection optical system 13 makes a scattered light beam travelling along the travelling direction of the fluid in the detection area (that is, the travelling direction of the particles) enter the beam splitter 17, out of scattered light beams emitted from the particles and the fluid in the flow passage 2a.

In the embodiment, as illustrated in FIG. 3, the travelling direction of the fluid (X direction) is equal to the direction of the optical axis of the detection optical system 13. Accordingly, the scattered light beam within a predetermined solid angle from the center of the detection area enters the beam splitter 17.

In this manner, out of the scattered light beams emitted from the particles in the flow passage 2a, the side scattered light beam travelling along the travelling direction (X direction) of the fluid in the detection area is detected. In addition, in the detection area, with the movement of the particles, the light path length as a distance between the particles and the beam splitter 17 changes. This change may become larger in the case where the scattered light beam by the particles is detected in the X direction than in the case where the same is detected in other directions (directions other than the X direction). This will be described later.

Meanwhile, the other of the light beams split by the beam splitter 11 enters the attenuator 14.

The attenuator 14 attenuates the intensity of the light beam at a predetermined ratio. The attenuator 14 may be a neutral density (ND) filter, for example. The beam splitter 11 and the attenuator 14 set the intensity of the light beam entering the diffraction optical system 15 to a predetermined value. In addition, the intensity of the reference light beam that is emitted from the diffraction optical system 15 and that enters the beam splitter 17 is set according to the size of the particles to be counted, the intensity of the scattered light beam, and the like. Further, the attenuation rate of the attenuator 14 and the like are set to achieve the intensity of the reference light beam.

The diffraction optical system 15 splits the light beam emitted from the attenuator 14 (that is, the other of the light beams split by the beam splitter 11) into a plurality of light beams travelling in a space. The mirror 16 reflects the plurality of light beams emitted from the diffraction optical system 15. The plurality of reflected light beams enters a predetermined incident surface of the beam splitter 17 (other than the incidence surface of the scattered light beams) as a plurality of reference light beams.

In the embodiment, the detection optical system 13, the diffraction optical system 15, and the mirror 16 are configured such that the wave front shape of scattered light beam by the particle and the wave front shape of any one of reference light beams approximately coincide with each other at the beam splitter 17. In the embodiment, the detection optical system 13 and the diffraction optical system 15 are configured to emit the scattered light beam and the reference light beams respectively as approximately parallel light beams. The wave front shapes of the scattered light beam and the reference light beams may be curved planes.

In addition, the detection optical system 13, the diffraction optical system 15, and the mirror 16 are configured such that their polarizing angles at the beam splitter 17 coincide with one another.

As described above, in the embodiment, to further enhance the degree of interference, the attenuator 14, the diffraction optical system 15, the mirror 16, and others, being arranged in the light path of the reference light beams, control the intensity, polarizing angle, and wave front shape of the reference light beams.

The beam splitter 17 superimposes the incident scattered light beam on the incident reference light beam in the space so that they interfere with each other to mutually strengthen or weaken. In this embodiment, the beam splitter 17 may be provided separately from the beam splitter 11. At the beam splitter 17, a phase difference between the scattered light beam and the reference light beam changes depending on changes in the light path length resulting from the movement of the particle in the detection area. In addition, as described later, the intensity of the interference light beam changes depending on the light beam passing through or reflected on the beam splitter 17. As described above, detecting the side scattered light beam travelling along the travelling direction of the fluid in the detection area allows changes to be large and rapid, as compared to the case in which the side scattered light beam is detected in other directions, with the movement of the particle in the detection area. Accordingly, the velocity at which the intensity of the interference light beam changes becomes high. Therefore, the intensity of the interference light beam changes depending on a cycle length (in other words, on a frequency) according to the velocity in the travelling direction of the fluid in the detection area (that is, the travelling direction of the particles). For the period during which no scattered light beam by the particle enters, the transmission component of the scattered light beam by the fluid and the reflection component of the reference light beam interfere with each other and are emitted from the beam splitter 17. Similarly, the reflection component of the scattered light beam by the fluid and the transmission component of the reference light beam interfere with each other and are emitted. In this case, the molecules of the fluid are extremely small in size and extremely large in number. Accordingly, the scattered lights by those molecules are random. As a result, changes in the interference light beams are smaller than changes in the interference light beams by the particle.

The condenser 18a condenses light beams emitted from an emission surface of the beam splitter 17. The condensed light beams enter the light receiving element 21a. The condenser 18b condenses the light beams emitted from another emission surface of the beam splitter 17. The condensed light beams enter the light receiving element 21b. The condensers 18a and 18b includes condensing lenses, for example.

Figure 4:
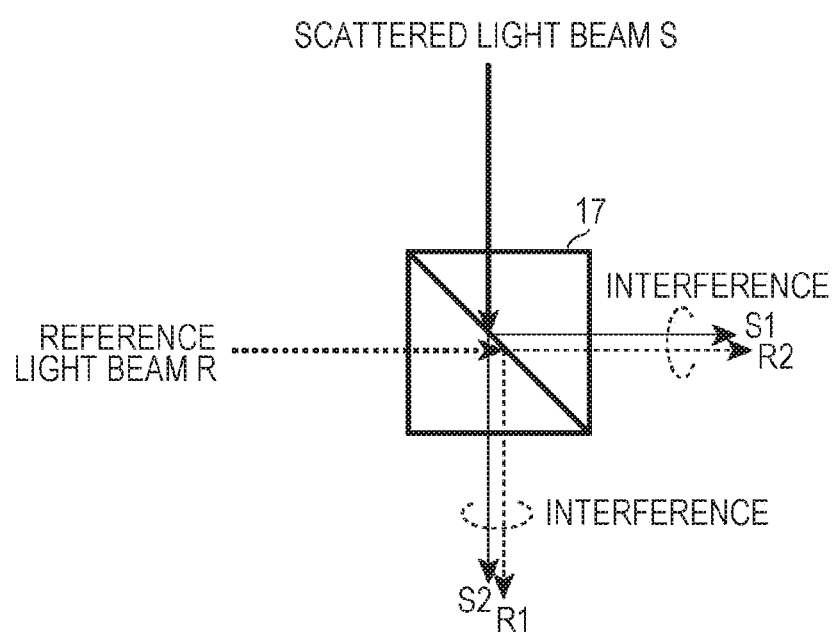
FIG. 4 describes light beam splitting by the beam splitter 17 illustrated in FIG. 1.

FIG. 4 describes light beam splitting by the beam splitter 17 illustrated in FIG. 1. As illustrated in FIG. 4, a scattered light beam S and reference light beams R enter the beam splitter 17. At this time, the travelling direction of a reflection component S1 of the scattered light beam S and the travelling direction of a transmission component R2 of any of the reference light beams R coincide with each other. Further, the travelling direction of a transmission component S2 of the scattered light beam S and the travelling direction of reflection component R1 of any of the reference light beams R coincide with each other. Therefore, the beam splitter 17 emits a first interference light beam generated by the reflection component S1 of the scattered light beam S and the transmission component R2 of the reference light beam R and a second interference light beam generated by the transmission component S2 of the scattered light beam S and the reflection component R1 of the reference light beam R. The first interference light beam and the second interference light beam enter the light receiving elements 21a and 21b of the detector 4 via the condensers 18a and 18b, respectively.

The scattered light beam S and the reference light beam R enter the light splitting surface of the beam splitter 17 at an angle of approximately 45 degrees. Accordingly, the transmission components S2 and R2 have the same phases as those of the scattered light beam S and the reference light beam R, respectively. Meanwhile, the phases of the reflection components S1 and R1 lag by 90 degrees the scattered light beam S and the reference light beam R, respectively. Therefore, the intensities of the first interference light beam and the second interference light beam change in opposite phases as described later.

In addition, preferably, the ratio of the transmission component to the reflection component in the beam splitter 17 is 50:50. However, the ratio may be uneven such as 60:40. When the ratio of the transmission component to the reflection component in the beam splitter 17 is uneven, the gains of amplifiers 22a and 22b are set depending on the ratio of the transmission component to the reflection component in the beam splitter 17. The gains of amplifiers 22a and 22b are set so that the transmission component of the reference light beam in an electrical signal V1 and the reflection component of the reference light beam in an electrical signal V2 become equal.

A beam damper 19 absorbs the light beam having passed through the flow cell 2. With the light beam absorption by the beam damper 19, the influence on the optical system 3 caused by irregular light reflection, leakage, and others can be suppressed.

The detector 4, using the light receiving elements 21a and 21b, receives the interference light beams emitted from the beam splitter 17 and outputs a detection signal Vo corresponding to the difference between the interference light beams. In the embodiment, as illustrated in FIG. 1, the detector 4 includes the light receiving elements 21a and 21b, the amplifiers 22a and 22b, and a difference calculator 23.

As examples of the light receiving elements 21a and 21b, there may be include multi-divided photo detectors such as a photodiode array or a phototransistor array, and image sensors such as charge coupled devices (CCD). Each of the light receiving elements includes a plurality of light receivers and outputs electrical signals corresponding to a light beam that enters one of the light receivers. The amplifiers 22a and 22b amplify the electrical signals output from the light receivers of the light receiving elements 21a and 21b at predetermined gains. The difference calculator 23 calculates the difference between the electrical signal V1 corresponding to the first interference light beam received by a light receiver of the light receiving element 21a and the electrical signal V2 corresponding to the second interference light beam received by a light receiver of the light receiving element 21b. Here, the light receiver of the light receiving element 21b corresponds to the light receiver of the light receiving element 21a. That is, the second interference light beam that enters the light receiver of the light receiving element 21b corresponds to the first interference light beam that enters the light receiver of the light receiving element 21a. The calculation result by the electrical signal V1 corresponding to the first interference light beam received by a light receiver of the light receiving element 21a and the electrical signal V2 corresponding to the second interference light beam received by a light receiver of the light receiving element 21b is outputted as the detection signal Vo.

Figure 5:
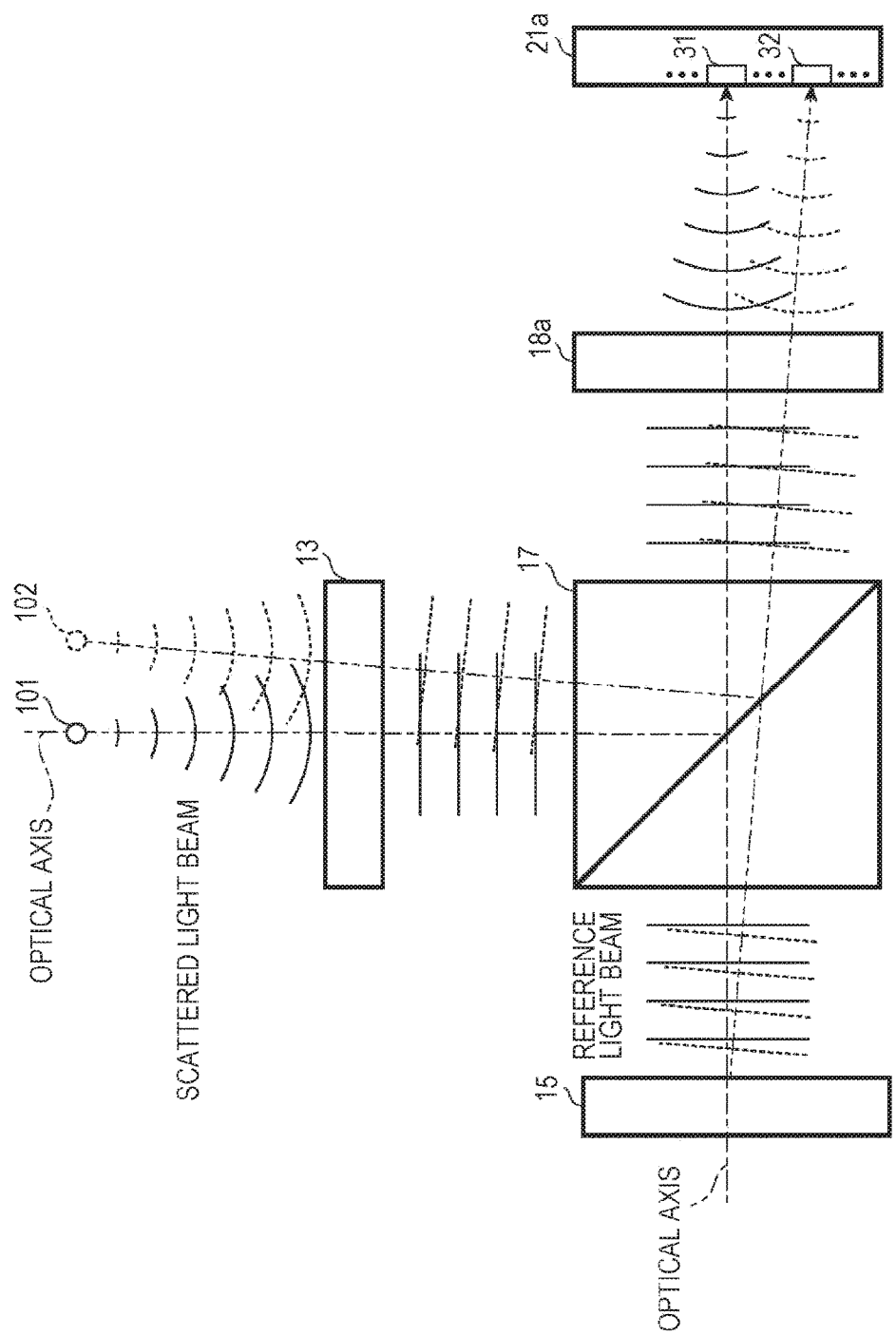
FIG. 5 describes interfering light in the particle counter illustrated in FIG. 1.

FIG. 5 describes the interference light beam in the particle counter illustrated in FIG. 1.

In the first embodiment, the diffraction optical system 15 includes a diffraction grating and a condensing lens arranged at the subsequent stage of the diffraction grating. The diffraction grating splits the light beam emitted from the attenuator 14 into a plurality of light beams travelling in the space. The condensing lens changes the wave fronts of the plurality of split light beams into parallel light beams. The diffraction grating includes a multi-pin hole, a multi-slit, or a lens array, for example. That is, in this diffraction grating, unit structures such as pin holes, slits, or lenses are arranged in a one-dimensional or two-dimensional manner. A condensing lens may be further arranged at the preceding stage of the diffraction grating. The condensing lens may make the light beam from the attenuator 14 enter the diffraction grating. These condensing lenses may include plane-convex lenses, double-convex lenses, or the like, for example. Alternatively, these condensing lenses may include aspherical lenses, spherical lenses, or cylindrical lenses shaped according to the size of the diffraction grating or the predetermined energy density. The diffraction optical system 15 as described above is configured to emit the plurality of reference light beams corresponding to the plurality of unit structures (pin holes, slits, lenses, or the like). These reference light beams enter the beam splitter 17 via the mirror 16. Referring to FIG. 5, the wave fronts of the reference light beams shown by solid lines are wave fronts obtained by the unit structures on the optical axis. The wave fronts of the reference light beams shown by broken lines are wave fronts obtained by the unit structures outside the optical axis. In this manner, the diffraction optical system 15 generates the plurality of reference light beams that travels at different angles with respect to the optical axis.

The light receiving element 21a includes a plurality of light receivers 31, 32, . . . corresponding to the plurality of reference light beams described above. The interference light beam generated by interference between the scattered light beam and any of the reference light beams is received by any of the light receivers 31, 32, . . . corresponding to the reference light beam. Then, an electrical signal corresponding to the received interference light beam is outputted. That is, the condenser 18a makes the interference light beam enter any of the plurality of light receivers 31, 32, . . . . In this case, the light receiver receiving the interference light beam corresponds to the distance between the optical axis and the particle in the detection area. Specifically, the scattered light beam by the particle interferes with the reference light beam from one of the unit structures in the diffraction optical system 15. In this case, the distance between the optical axis and the particle in the detection area correspond to the distance between the optical axis and the unit structure in the diffraction optical system 15. The interference light beam generated by the interference enters any of the light receivers 31, 32, . . . corresponding to the reference light beam from the unit structure. In this manner, the unit structures of the diffraction grating in the diffraction optical system 15 and the light receivers in the light receiving element 21a are associated with each other on a one-to-one basis or a one-to-many basis.

For example, FIG. 5 illustrates by solid lines the wave front of the interference light beam generated by the scattered light beam by the particle 101 on the optical axis in the detection area and the reference light beam from the unit structure on the optical axis as the center of the diffraction optical system 15. The interference light beam enters the light receiver 31 on the optical axis via the condenser 18a. FIG. 5 also illustrates by broken lines the wave front of the interference light beam generated by the scattered light beam by a particle 102 at a predetermined distance from the optical axis in the detection area and the reference light beam from the unit structure of the diffraction optical system 15 corresponding to the position of the particle 102. The interference light beam enters the light receiver 32 corresponding to the reference light beam via the condenser 18a.

FIG. 5 does not illustrate the condenser 18b or the light receiving element 21b. However, the condenser 18b and the light receiving element 21b have the same functions as those of the condenser 18a and the light receiving element 21a.

The gains of the amplifiers 22a and 22b corresponding to the light receiving elements are adjusted in advance. By this adjustment, when the interference light beam does not include the component of the scattered light beam by the particle (but includes only the component of the scattered light beam by the fluid and the reference light beam component), the voltages of the electrical signal V1 and the electrical signal V2 from the pairs of the light receivers of the light receiving element 21a and the light receivers of the light receiving element 21b are equal. Alternatively, only either the amplifier 22a or 22b may be provided. In this case, the gain of the provided amplifier is adjusted such that the voltages of the electrical signals from the pairs are equal. Still alternatively, none of the amplifiers 22a and 22b may be provided as far as the voltage of the electrical signal from the light receiving element 21a and the voltage of the electrical signal from the light receiving element 21b are equal.

Figure 6:
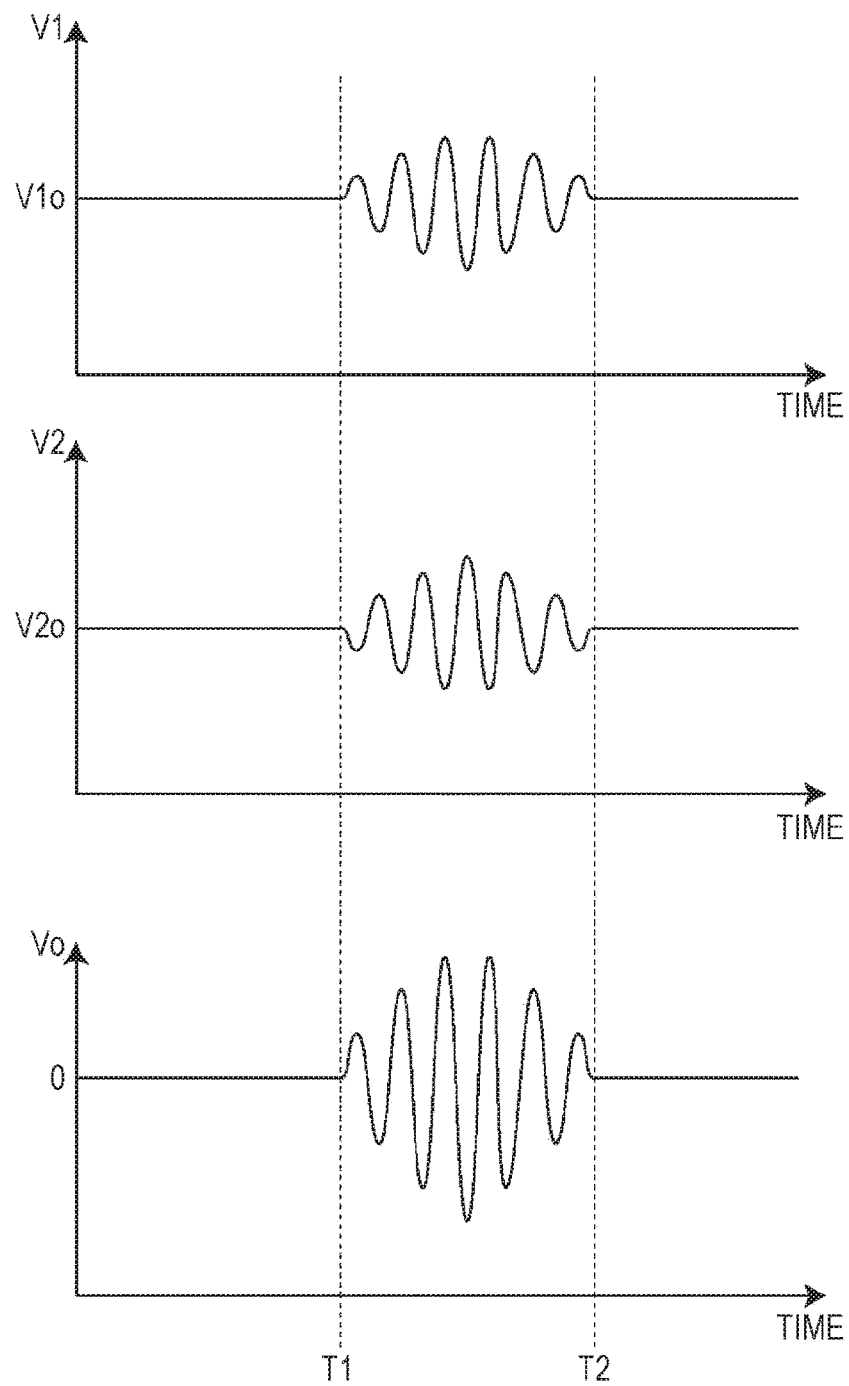
FIG. 6 is a timing chart for describing detection signals obtained by a detector 4 illustrated in FIG. 1.

FIG. 6 is a timing chart for describing detection signals obtained by the detector 4 illustrated in FIG. 1.

When a particle passes through the detection area during a period of time T1 to time T2, a scattered light beam is generated by the particle in that period. Then, as the particle moves in the travelling direction (X direction) in the detection area, the light path length from the particle to the light splitting surface of the beam splitter 17 changes. Accordingly, the phase difference between the scattered light beam by the particle and the reference light beam changes. As a result, the phase difference between the light beams causes the intensity of the interference light beam (amplitude) to strengthen or weaken mutually.

Therefore, as illustrated in FIG. 6, in the period during which the particle passes through the detection area, the electrical signal V1 changes positively or negatively with respect to a reference depending on the degree of interference. The reference is a voltage V1o without the particle. Similarly, in the period during which the particle passes through the detection area, the electrical signal V2 changes positively or negatively with respect to a reference depending on the degree of interference. The reference is a voltage V2o without the particle. However, the AC components of the electrical signals V1 and V2 in that period are opposite in phase.

The reference voltages V1o and V2o of the electrical signals V1 and V2 outputted from the amplifiers 22a and 22b are equal. Accordingly, as illustrated in FIG. 6, the detection signal Vo obtained by the difference calculator 23 has an AC component with a larger amplitude (about double) than the AC component resulting from the interferences of the electrical signals V1 and V2 in the period during which the particle passes through the detection area. In addition, the detection signal Vo has a voltage of almost zero at all other times than that period.

In the embodiment of the present disclosure, the scattered light beam travelling along the travelling direction (X direction) of the fluid in the detection area is detected. Accordingly, when the particle passes through the detection area, a change in the light path length becomes larger. The movement distance of the particle in the period of time T1 to time T2 constitutes the change in light path length between the particle and the light splitting surface of the beam splitter 17. Accordingly, the number of changes in interference increases as compared to the case in which the scattered light beam by the particle is detected in other directions (than the X direction). That is, when the velocity of change in the intensity of the interference light beam becomes high, the number of phase rotations of the interference light beam increases. This means that the number of waves in the electrical signals output from the light receivers of the light receiving elements 21a and 21b increases in the period of time T1 to time T2. The increasing the number of waves in the electrical signals output makes it easier to detect the signals. Accordingly, it is possible to improve the S/N ratio. However, there is no limitation in the direction of detection of the scattered light beam as long as the scattered light beam is detected in the direction.

The scattered light beam (background light beam) from the liquid as a fluid medium is generated in the entire detection area. Further, there exist background light beams from different positions. However, the influences from the background light beams are canceled out by the difference calculation. Accordingly, the AC component of the detection signal Vo resulting from the interference of the background light beam is smaller than the AC component of the detection signal Vo resulting from the interference of the scattered light beam by the particle.

In the embodiment, the particle size of the particles to be counted is smaller than the wavelength of the light emitted from the light source 1. Accordingly, the intensity of the scattered light beam caused by Rayleigh scattering is proportional to the sixth power of the particle size. In contrast, the intensity of the interference light beam generated by the scattered light beam and the reference light beam is proportional to the third power of the particle size. Specifically, the particle size and intensity I of the interference light beam satisfies the relational equation ($I \propto Er \cdot ED1 \cdot (D1/D0)^3$). In the equation, $D0$ and $D1$ denote the particle size, $Er$ the electric field intensity of the reference light beam, and $ED1$ the electric field intensity of the scattered light beam by the particle $D1$. Accordingly, even when the particle size is smaller in the detection of the interference light beam than in the direct detection of the scattered light beam, the degree of decrease in the intensity of the detected light beam is smaller.

The difference between the maximum value and the minimum value of the intensity of the interference light beam generated by the scattered light beam and the reference light beam (the difference in the intensity of the interference light beam between when the phase difference between the scattered light beam and the reference light beams is zero degree and when the phase difference between the scattered light beam and the reference light beams is 180 degrees) is proportional to the product of an electric field intensity $Er$ of the reference light beam and an electric field intensity $Es$ of the scattered light beam. Enhancing the intensities of the scattered light and the reference light beam may obtain an interference light beam with a sufficient intensity and a detection signal with a sufficiently large amplitude. The value of the intensity of the reference light beam is set such that the detection signal is favorably processed depending on the dynamic ranges of the detector 4, the filter 5, and the counting unit 6.

For example, when intensity Is of a scattered light beam by a particle with a particle size of 20 nm is $7.0 \times 10^{-6}$ μW, the relational equation ($I = 0.5 \cdot c \cdot \epsilon \cdot Es^2$) of intensity I of the scattered light beam per unit area obtained by converting the intensity Is, and the intensity of the scattered light beam and the electric field intensity gives about $5.8 \times 10^{-3}$ V/m as electric field intensity Es of the scattered light beam. In the equation, c represents the velocity of light (m/s), and $\epsilon$ the electric permittivity of the air (F/m). Meanwhile, when intensity Ir of the reference light beam is 1.2 μW, about 2.4 V/m can be obtained as electric field intensity Er of the reference light beam. In addition, when the scattered light beam and the reference light beam interfere with each other in the entire wave fronts, about $1.2 \times 10^{-2}$ μW can be obtained as the difference between the intensities of the interference light beams ($2 \cdot c \cdot \epsilon \cdot Es \cdot Er \cdot$unit area). That is, the difference between the intensities of the interference light beams is about 1600 times larger than the intensity of the scattered light beam. This means that the difference between the intensities of the interference light beams is amplified to the level equivalent to the intensity of the scattered light beam by a particle with a particle size of 70 nm.

The filter 5 subjects the detection signal Vo generated by the detector 4 to a filtering process. Specifically, first, the electrical signals V1 and V2 are generated corresponding to the light receivers of the light receiving elements 21a and 21b. Then, the electrical signals V1 and V2 are subjected to difference processing corresponding to the light receivers to generate the detection signal Vo. The filter 5 subjects the detection signal Vo to filtering process. At this time, the filter 5 lets pass the frequency component (that is, the frequency component of intensity change of the interference light beam) corresponding to the velocity of the fluid in the flow passage 2a (that is, the moving velocity of the particle), and attenuates the frequency components other than the frequency component corresponding to the travelling velocity of the fluid. Accordingly, the noise component of the detection signal Vo may be attenuated. This makes higher the S/N ratio of the detection signal Vo. The passband frequency is determined in advance by the moving velocity of the particle (that is, the amount of change in the light path length caused by the movement of the particle in the period of time T1 to time T2), the wavelength of the measurement light beam (that is, the wavelength of the light source 1), and the like. The filter 5 includes a bandpass filter. Alternatively, the filter 5 may be a low-pass filter when the frequency of the noise is higher than the frequency of the interference light beam. Meanwhile, the filter 5 may be a high-pass filter when the frequency of the noise is lower than the frequency of the interference light beam.

When the intensity of the reference light beam is constant, the detection signal Vo changes according to the intensity of the scattered light beam. Accordingly, the counting unit 6 counts the particles on the basis of the detection signals Vo generated corresponding to the light receivers of the light receiving elements 21*a* and 21*b*. Specifically, the counting unit 6 counts the particles in the particle size sections on the basis of the plurality of detection signals Vo generated corresponding to the plurality of light receivers of the light receiving elements 21*a* and 21*b* and calculates the total sum of the count values. In the embodiment, the counting unit 6 counts the particles on the basis of the detection signals Vo after the filtering process by the filter 5. For example, out of the components of the detection signals Vo based on the intensities of the interference light beams according to the particle sizes of the particles, the counting unit 6 detects the AC components continuous during the foregoing period (that is, the frequency components of the interference light beams). Accordingly, the counting unit 6 compares the amplitudes to predetermined thresholds decided by the particle size. Then, the counting unit 6 differentiates between the particles by the particle size and counts one particle.

Next, operations of the particle counter according to the first embodiment will be explained.

The light source 1 emits a laser beam as a light beam. The beam splitter 11 splits the light beam into two. One of the light beams is attenuated by the attenuator 14. After that, the attenuated light beam enters the diffraction optical system 15. The diffraction optical system 15 splits the light beam into a plurality of light beams travelling in the space. The plurality of light beams is emitted as a plurality of reference light beams, and enters, as approximately parallel light beams, the beam splitter 17 through the mirror 16.

Meanwhile, the irradiation optical system 12 makes the other split light beam enter the detection area of the flow cell 2 as a measurement light beam. When the particle passes through the detection area, the particle generates a scattered light beam during the period of passage through the detection area. The scattered laser beam travelling along the travelling direction (X direction) of the fluid in the flow passage 2*a* of the flow cell 2 enters the detection optical system 13. The detection optical system 13 makes the scattered light beam enter the beam splitter 17 as approximately parallel light beams.

As described above, in the period during which the particle passes through the detection area, the plurality of reference light beams and the scattered light beam by the particle enter the beam splitter 17, and the beam splitter 17 emits the interference light beam generated by any one of the reference light beams and the scattered light beam according to the passage position of the particle.

In the period during which the particle passes through the detection area, the beam splitter 17 emits the interference light beams. The interference light beams are received by the light receivers corresponding to the reference light beams (that is, the reference light beams corresponding to the passage positions of the particles) in the light receiving elements 21*a* and 21*b*. Then, the detector 4 outputs the electrical signals corresponding to the intensities of the received interference light beams as detection signals Vo. In particular, in the first embodiment, the detection signals Vo are generated based on the difference between the first interference light beam and the second interference light beam being opposite in phases to each other. Accordingly, the detection signals Vo of the AC components having an amplitude about two times larger than the electrical signals V1 and V2 can be obtained.

The filter 5 subjects the detection signals to the foregoing filtering process. Then, the counting unit 6 counts the particles on the basis of the detection signals after the filtering process.

As described above, according to the first embodiment, the light beam emitted from the light source 1 is split into a plurality of light beams. The irradiation optical system 12 irradiates the fluid in the flow passage 2*a* with one of the plurality of split light beams from a direction different from the flowing direction of the fluid. The irradiation to the fluid forms the detection area. The detection optical system 13 makes the scattered light beam with a different direction from the optical axis of the irradiation optical system 12 enter the beam splitter 17, out of the scattered light beams by the particle contained in the fluid in the detection area. Meanwhile, the diffraction optical system 15 and the mirror 16 split another of the plurality of light beams into a plurality of light beams travelling in the space. The plurality of split light beams enters the beam splitter 17 as a plurality of reference light beams. The detector 4 includes the plurality of light receivers corresponding to the plurality of reference light beams. The interference light beams generated by the scattered light beams and the reference light beams obtained by the beam splitter 17 each are received by the light receiver of the light receiving element corresponding to the reference light beam. Then, the detection signals corresponding to the interference light beams are generated. The counting unit 6 counts the particles on the basis of the detection signals.

Accordingly, the passage of the particle is detected on the basis of the interference light beams resulting from passage of particle in the detection area. Therefore, it is possible to count small-diameter particles in the fluid with an improved S/N ratio as compared to the case of detecting the scattered light beams.

In addition, according to the first embodiment, the diffraction optical system 15 generates a plurality of reference light beams by the use of a plurality of unit structures corresponding to the passage positions of the particles in the detection area. Accordingly, it is possible to obtain interference light beams with the intensities for counting the particles from the scattered light beams by the particles passing through positions separated from the optical axis in the detection area. As a result, the counting efficiency of the particles can be improved.

Second Embodiment

In the first embodiment, the first interference light beam and the second interference light beam are received as interference light beams generated by the scattered light beam by the particle and the reference light beam. In addition, the difference between their electrical signals V1 and V2 is used as the detection signal Vo. In the second embodiment, instead of this, the electrical signal from either the first interference light beam or the second interference light beam is used as the detection signal Vo. In this case, the detection signal Vo may also contain an AC component resulting from the interference light beam generated by the scattered light beam by the particle and the reference light beam. Accordingly, the particles can be counted in the same manner. In this case, only one light receiving element may be provided.

Other components of a particle counter according to the second embodiment are the same as those of the first embodiment, and descriptions thereof will be omitted.

The foregoing embodiments are preferred examples of embodiments. However, embodiments are not limited to the foregoing ones. The embodiments described above can be modified and changed in various manners without deviating from the gist of the embodiments.

For example, in the first and second embodiments, one mirror 16 is used as illustrated in FIG. 1. Alternatively, three mirrors may be used to adjust three-dimensionally the direction of the light path. In addition, in the first and second embodiments, the scattered light beam by the particle and the reference light beams are superimposed by the use of the beam splitter 17. Alternatively, a polarization prism may be used instead of the beam splitter 17.

In the first and second embodiments, the filter 5 may be omitted when the noise component of the detection signal Vo is small. In that case, the detection signal Vo is inputted directly into the counting unit 6.

In the first and second embodiments, the light source 1 emits a single-mode and high-coherence laser beam. Alternatively, a light source emitting a multi-mode and relatively low-coherence laser beam may be used instead of the light source 1. However, it is preferred to use a light source having energy distribution in which interference between the scattered light beam by the particle and the reference light beams takes place at any position in the detection area. The light source 1 is not limited to a light source emitting a laser beam. Instead of a laser beam, any other light beam in which the difference in light path length between the reference light beam and the scattered light beam by the particle falls within the light beam coherence length of the light source 1 such as an LED light beam may be used.

In the first and second embodiments, the filter 5 and the counting unit 6 may be analog circuits or digital circuits. When the filter 5 and the counting unit 6 are digital circuits, the detection signal Vo is subjected to analog-digital conversion at the preceding stage of the filter 5.

In the first and second embodiments, as illustrated in FIG. 1, a Mach-Zehnder interference optical system in which the splitting of light beams and the superimposition of light beams are performed by the different beam splitters 11 and 17. Alternatively, a Michelson interference optical system or any other type interference optical system may be used instead.

In addition, the particle counters according to the first and second embodiments are liquid-borne particle counters (counters for liquid-borne particles). Alternatively, the particle counters according to the first and second embodiments may be airborne particle counters (counters for air-borne particles).

The particle counters according to the embodiments of the present disclosure may be the following first to fifth particle counters:

The first particle counter includes: a light source; a light superimposition unit that superimposes spatially two light beams; an irradiation optical system that irradiates a fluid flowing in a flow passage with one of a plurality of light beams obtained by splitting a light beam from the light source to form a detection area; a detection optical system that makes a scattered light beam with a different direction from the optical axis of the irradiation optical system enter the light superimposition unit, out of scattered light beams by a particle contained in the fluid in the detection area; a reference optical system that splits spatially another one of the plurality of light beams into a plurality of light beams and makes the plurality of light beams enter the light superimposition unit as a plurality of reference light beams; a detector including a plurality of light receivers corresponding to the plurality of reference light beams, the detector receiving interference light beams generated by the scattered light beam and the reference light beams obtained by the light superimposition unit by the light receivers corresponding to the reference light beams and generating detection signals corresponding to the interference light beams; and a counting unit that counts the particles on the basis of the detection signals.

The second particle counter is the first particle counter configured such that the reference optical system is a diffraction grating that splits spatially another one of the plurality of light beams into a plurality of light beams.

The third particle counter is the first or second particle counter configured such that the detection optical system and the reference optical system emit the scattered light beam and the plurality of reference light beams such that a wave front shape of the scattered light beam by the particle in the detection area and a wave front shape of any of the plurality of reference light beams approximately coincide with each other.

The fourth particle counter is any one of the first to third particle counters, further including a condenser that makes the interference light beam enter, out of the plurality of light receivers, the light receiver corresponding to the distance from the optical axis of the particle in the detection area.

The fifth particle counter is any one of the first to fourth particle counters configured such that the light superimposition unit is a beam splitter that generates a first interference light beam composed of a transmission component of the scattered light beam and a reflection component of the reference light beam and a second interference light beam composed of a reflection component of the scattered light beam and a transmission component of the reference light beam, the detector receives the first interference light beam and the second interference light beam by any of light receivers in two light receiving elements each including a plurality of light receivers corresponding to the plurality of reference light beams, and generates the difference between an electrical signal corresponding to the first interference light beam and an electrical signal corresponding to the second interference light beam as the detection signal.

The foregoing detailed description has been presented for the purposes of illustration and description. Many modifications and variations are possible in light of the above teaching. It is not intended to be exhaustive or to limit the subject matter described herein to the precise form disclosed. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims appended hereto.

The present disclosure is applicable to particle counters for chemical solutions, for example.

What is claimed is:
1. A particle counter comprising:
a light source;
a light superimposition unit configured to superimpose two light beams travelling in a space;

an irradiation optical system configured to irradiate a fluid flowing in a flow passage with one of a plurality of light beams obtained by splitting a light beam from the light source to form a detection area;
a detection optical system configured to make a scattered light beam with a different direction from the optical axis of the irradiation optical system enter the light superimposition unit, out of scattered light beams scattered by a particle contained in the fluid in the detection area;
a reference optical system comprising a diffraction optical system configured to split another one of the plurality of light beams into a plurality of light beams travelling in a space, the reference optical system configured to make the split light beams enter the light superimposition unit as reference light beams;
a detector comprising light receivers, each light receiver being corresponding to each of the reference light beams, and configured to generate detection signals corresponding to an interference light beam received by the light receiver; and
a counting unit configured to count the particles on the basis of the detection signals, wherein
the interference light beam is generated by interference between the scattered light beam and one of the reference light beams that enter the light superimposition unit, and is received by the light receiver corresponding to the reference light beam.

2. The particle counter according to claim 1, wherein the diffraction optical system comprises a diffraction grating configured to split the other one of the plurality of light beams into the plurality of light beams travelling in the space.

3. The particle counter according to claim 1, wherein the detection optical system and the reference optical system emit the scattered light beam and the plurality of reference light beams respectively such that a wave front shape of the scattered light beam scattered by a particle in the detection area and a wave front shape of one of the plurality of reference light beams approximately coincide with each other.

4. The particle counter according to claim 2, wherein the detection optical system and the reference optical system emit the scattered light beam and the plurality of reference light beams respectively such that a wave front shape of the scattered light beam scattered by the particle in the detection area and a wave front shape of one of the plurality of reference light beams approximately coincide with each other.

5. The particle counter according to claim 1, further comprising:
a condenser configured to make the interference light beam enter the light receiver corresponding to a distance from the optical axis to the particle in the detection area.

6. The particle counter according to claim 2, further comprising:
a condenser configured to make the interference light beam enter the light receiver corresponding to a distance from the optical axis to the particle in the detection area.

7. The particle counter according to claim 3, further comprising:
a condenser configured to make the interference light beam enter the light receiver corresponding to a distance from the optical axis to the particle in the detection area.

8. The particle counter according to claim 4, further comprising:
a condenser configured to make the interference light beam enter the light receiver corresponding to a distance from the optical axis to the particle in the detection area.

9. The particle counter according to claim 1, wherein
the light superimposition unit comprises a beam splitter configured to generate a first interference light beam and a second interference light beam, the first interference light beam being comprised of a transmission component of the scattered light beam and a reflection component of one of the reference light beams, the second interference light beam being comprised of a reflection component of the scattered light beam and a transmission component of one of the reference light beams,
the detector comprises two light receiving elements each comprising the plurality of light receivers,
each light receiver included in one of the light receiving elements receives the first interference light beam,
each light receiver included in the other of the light receiving elements receives the second interference light beam, and
the difference between an electrical signal corresponding to the received first interference light beam and an electrical signal corresponding to the received second interference light beam is generated as the detection signal.

10. The particle counter according to claim 2, wherein
the light superimposition unit comprises a beam splitter configured to generate a first interference light beam and a second interference light beam, the first interference light beam being comprised of a transmission component of the scattered light beam and a reflection component of one of the reference light beams, the second interference light beam being comprised of a reflection component of the scattered light beam and a transmission component of one of the reference light beams,
the detector comprises two light receiving elements each comprising the plurality of light receivers,
each light receiver included in one of the light receiving elements receives the first interference light beam,
each light receiver included in the other of the light receiving elements receives the second interference light beam, and
the difference between an electrical signal corresponding to the received first interference light beam and an electrical signal corresponding to the received second interference light beam is generated as the detection signal.

11. The particle counter according to claim 3, wherein
the light superimposition unit comprises a beam splitter configured to generate a first interference light beam and a second interference light beam, the first interference light beam being comprised of a transmission component of the scattered light beam and a reflection component of one of the reference light beams, the second interference light beam being comprised of a reflection component of the scattered light beam and a transmission component of one of the reference light beams,
the detector comprises two light receiving elements each comprising the plurality of light receivers,
each light receiver included in one of the light receiving elements receives the first interference light beam, each light receiver included in the other of the light receiving elements receives the second interference light beam, and the difference between an electrical signal corresponding to the received first interference light beam and an electrical signal corresponding to the received second interference light beam is generated as the detection signal.

12. The particle counter according to claim 4, wherein the light superimposition unit comprises a beam splitter configured to generate a first interference light beam and a second interference light beam, the first interference light beam being comprised of a transmission component of the scattered light beam and a reflection component of one of the reference light beams, the second interference light beam being comprised of a reflection component of the scattered light beam and a transmission component of one of the reference light beams, the detector comprises two light receiving elements each comprising the plurality of light receivers, each light receiver included in one of the light receiving elements receives the first interference light beam, each light receiver included in the other of the light receiving elements receives the second interference light beam, and the difference between an electrical signal corresponding to the received first interference light beam and an electrical signal corresponding to the received second interference light beam is generated as the detection signal.

13. The particle counter according to claim 5, wherein the light superimposition unit comprises a beam splitter configured to generate a first interference light beam and a second interference light beam, the first interference light beam being comprised of a transmission component of the scattered light beam and a reflection component of one of the reference light beams, the second interference light beam being comprised of a reflection component of the scattered light beam and a transmission component of one of the reference light beams, the detector comprises two light receiving elements each comprising the plurality of light receivers, each light receiver included in one of the light receiving elements receives the first interference light beam, each light receiver included in the other of the light receiving elements receives the second interference light beam, and the difference between an electrical signal corresponding to the received first interference light beam and an electrical signal corresponding to the received second interference light beam is generated as the detection signal.

14. The particle counter according to claim 6, wherein the light superimposition unit comprises a beam splitter configured to generate a first interference light beam and a second interference light beam, the first interference light beam being comprised of a transmission component of the scattered light beam and a reflection component of one of the reference light beams, the second interference light beam being comprised of a reflection component of the scattered light beam and a transmission component of one of the reference light beams, the detector comprises two light receiving elements each comprising the plurality of light receivers, each light receiver included in one of the light receiving elements receives the first interference light beam, each light receiver included in the other of the light receiving elements receives the second interference light beam, and the difference between an electrical signal corresponding to the received first interference light beam and an electrical signal corresponding to the received second interference light beam is generated as the detection signal.

15. The particle counter according to claim 7, wherein the light superimposition unit comprises a beam splitter configured to generate a first interference light beam and a second interference light beam, the first interference light beam being comprised of a transmission component of the scattered light beam and a reflection component of one of the reference light beams, the second interference light beam being comprised of a reflection component of the scattered light beam and a transmission component of one of the reference light beams, the detector comprises two light receiving elements each comprising the plurality of light receivers, each light receiver included in one of the light receiving elements receives the first interference light beam, each light receiver included in the other of the light receiving elements receives the second interference light beam, and the difference between an electrical signal corresponding to the received first interference light beam and an electrical signal corresponding to the received second interference light beam is generated as the detection signal.

16. The particle counter according to claim 8, wherein the light superimposition unit comprise a beam splitter configured to generate a first interference light beam and a second interference light beam, the first interference light beam being comprised of a transmission component of the scattered light beam and a reflection component of one of the reference light beams, the second interference light beam being comprised of a reflection component of the scattered light beam and a transmission component of one of the reference light beams, the detector comprises two light receiving elements each comprising the plurality of light receivers, each light receiver included in one of the light receiving elements receives the first interference light beam, each light receiver included in the other of the light receiving elements receives the second interference light beam, and the difference between an electrical signal corresponding to the received first interference light beam and an electrical signal corresponding to the received second interference light beam is generated as the detection signal.

17. A particle counter comprising:

a light source;

a light superimposition unit configured to superimpose two light beams travelling in a space;

an irradiation optical system configured to irradiate a fluid flowing in a flow passage with one of a plurality of light beams obtained by splitting a light beam from the light source to form a detection area;

a detection optical system configured to make a scattered light beam with a different direction from the optical axis of the irradiation optical system enter the light superimposition unit, out of scattered light beams scattered by a particle contained in the fluid in the detection area;

a reference optical system configured to split another one of the plurality of light beams into a plurality of reference light beams travelling in a space and makes the reference light beams enter the light superimposition unit;

a detector comprising light receivers, each light receiver being corresponding to each of the reference light beams, and configured to generate detection signals corresponding to an interference light beam received by the light receiver; and a counting unit configured to count the particles on the basis of the detection signals, wherein the interference light beam is generated by interference between the scattered light beam and one of the reference light beams that enter the light superimposition unit, and is received by the light receiver corresponding to the reference light beam, and the reference optical system comprises a diffraction grating configured to split the other one of the plurality of light beams into a plurality of light beams travelling in a space.

18. A particle counter comprising:

a light source;

a light superimposition unit configured to superimpose two light beams travelling in a space;

an irradiation optical system configured to irradiate a fluid flowing in a flow passage with one of a plurality of light beams obtained by splitting a light beam from the light source to form a detection area;

a detection optical system configured to make a scattered light beam with a different direction from the optical axis of the irradiation optical system enter the light superimposition unit, out of scattered light beams scattered by a particle contained in the fluid in the detection area;

a reference optical system configured to split another one of the plurality of light beams into a plurality of reference light beams travelling in a space and makes the reference light beams enter the light superimposition unit;

a detector comprising light receivers, each light receiver being corresponding to each of the reference light beams, and configured to generate detection signals corresponding to an interference light beam received by the light receiver; and a counting unit configured to count the particles on the basis of the detection signals, wherein the interference light beam is generated by interference between the scattered light beam and one of the reference light beams that enter the light superimposition unit, and is received by the light receiver corresponding to the reference light beam, the light superimposition unit comprises a beam splitter configured to generate a first interference light beam and a second interference light beam, the first interference light beam being comprised of a transmission component of the scattered light beam and a reflection component of one of the reference light beams, the second interference light beam being comprised of a reflection component of the scattered light beam and a transmission component of one of the reference light beams, the detector comprises two light receiving elements each comprising the plurality of light receivers, each light receiver included in one of the light receiving elements receives the first interference light beam, each light receiver included in the other of the light receiving elements receives the second interference light beam, and the difference between an electrical signal corresponding to the received first interference light beam and an electrical signal corresponding to the received second interference light beam is generated as the detection signal.

* * * * *